(12) United States Patent
Norfray

(10) Patent No.: US 7,622,102 B2
(45) Date of Patent: *Nov. 24, 2009

(54) METHOD FOR MONITORING EARLY TREATMENT RESPONSE

(75) Inventor: Joseph F. Norfray, Glenview, IL (US)

(73) Assignee: Receptomon, LLC, Glenview, IL (US)

( * ) Notice: Subject to any disclaimer, the term of this patent is extended or adjusted under 35 U.S.C. 154(b) by 1089 days.

This patent is subject to a terminal disclaimer.

(21) Appl. No.: 11/053,059

(22) Filed: Feb. 8, 2005

(65) Prior Publication Data

US 2006/0177377 A1    Aug. 10, 2006

(51) Int. Cl.
*A61B 5/055*    (2006.01)
(52) U.S. Cl. .................. 424/9.3; 424/1.11; 424/1.65; 424/1.81; 424/9.1; 424/9.2
(58) Field of Classification Search ............ 424/1.11, 424/1.65, 1.69, 1.73, 1.81, 1.85, 1.89, 9.1, 424/9.2, 9.3, 9.31, 9.32, 9.322, 9.323, 9.34, 424/9.341, 9.35, 9.351, 9.36, 9.361, 9.362, 424/9.363, 9.364, 9.365, 9.37; 600/407, 600/410
See application file for complete search history.

(56) References Cited

U.S. PATENT DOCUMENTS

| | | | |
|---|---|---|---|
| 4,354,499 A | 10/1982 | Damadian | |
| 4,411,270 A | 10/1983 | Damadian | |
| RE32,619 E | 3/1988 | Damadian | |
| RE32,689 E | 6/1988 | Damadian | |
| 4,843,321 A | 6/1989 | Sotak | |
| 4,962,357 A | 10/1990 | Sotak | |
| 5,111,819 A | 5/1992 | Hurd | |
| 5,200,345 A | 4/1993 | Young | |
| 5,498,421 A | 3/1996 | Grinstaff et al. | |
| 5,578,921 A | 11/1996 | Morrell | |
| 5,585,118 A | 12/1996 | Stoll | |
| 5,617,861 A | 4/1997 | Ross et al. | |
| 5,887,588 A | 3/1999 | Usenius et al. | |
| 5,903,149 A | 5/1999 | Gonen et al. | |
| 6,046,589 A | 4/2000 | Lamerichs et al. | |
| 6,181,134 B1 | 1/2001 | Wald | |
| 6,280,383 B1 | 8/2001 | Damadian | |
| 6,347,239 B1 | 2/2002 | Arnold et al. | |
| 6,400,150 B1 | 6/2002 | Liu et al. | |
| 6,617,169 B2 | 9/2003 | Ke et al. | |
| 6,630,125 B2 | 10/2003 | DeGrado et al. | |
| 6,639,405 B2 | 10/2003 | Liu et al. | |
| 6,681,132 B1 | 1/2004 | Katz et al. | |
| 6,708,053 B1 | 3/2004 | Brooks et al. | |
| 6,756,063 B2 | 6/2004 | Kiss | |
| 6,819,952 B2 | 11/2004 | Pfefferbaum et al. | |
| 6,838,877 B2 | 1/2005 | Heid et al. | |
| 7,289,840 B2 * | 10/2007 | Norfray ............ | 600/410 |
| 2001/0003423 A1 | 6/2001 | Wald | |
| 2002/0142367 A1 | 10/2002 | Ke et al. | |
| 2002/0173713 A1 | 11/2002 | Pfefferbaum et al. | |
| 2003/0028093 A1 | 2/2003 | Ke et al. | |
| 2003/0199751 A1 | 10/2003 | Gonzalez et al. | |
| 2003/0208120 A1 | 11/2003 | Thomas et al. | |
| 2003/0214292 A1 | 11/2003 | Heid et al. | |
| 2004/0092809 A1 | 5/2004 | DeCharms | |
| 2005/0031620 A1 | 2/2005 | Thorpe et al. | |
| 2005/0107683 A1 | 5/2005 | Mountford et al. | |
| 2006/0035945 A1 | 2/2006 | Attardo et al. | |
| 2006/0064003 A1 | 3/2006 | Norfray | |
| 2006/0177378 A1 | 8/2006 | Norfray | |
| 2006/0222591 A1 | 10/2006 | Norfray | |
| 2007/0128114 A1 | 6/2007 | Norfray | |
| 2007/0218006 A1 | 9/2007 | Norfray | |

FOREIGN PATENT DOCUMENTS

WO    WO 2006/036288 A2    4/2006
WO    WO 2006/086159 A2    8/2006

(Continued)

OTHER PUBLICATIONS

Becker et al., "Intracellular Compartments: The endoplasmic reticulum, Golgi Complex, Lysosomes, and Peroxisomes", *The World of the Cell, Third Edition*, The Benjamin/Cummings Publishing Company, Ch. 9, pp. 229-270 (1996).

(Continued)

*Primary Examiner*—D L Jones
(74) *Attorney, Agent, or Firm*—Leydig, Voit & Mayer, Ltd.

(57) ABSTRACT

Disclosed is a method for monitoring early treatment response of a cancer treatment comprising measuring by magnetic resonance spectroscopy (MRS), for example, proton MRS, the amount of Choline present in the tissue adjoining or surrounding the cancerous tissue before and after treatment; the treatment comprises administration of an angiogenesis inhibitor, for example, a VEGF inhibitor, whereby a decrease in the amount of Choline after treatment is indicative of a positive response. The decrease in the amount of Choline represents the decrease in the internal cell membrane as a result of down regulation of the organelles and their secretory granules and their transport vesicles. Disclosed also is a method for determining effectiveness of an angiogenesis inhibitor in the treatment of cancer. Also disclosed are methods of monitoring early treatment response in diseases where an angiogenesis effector, i.e., an inhibitor or promoter of angiogenesis, is employed.

42 Claims, 2 Drawing Sheets

FOREIGN PATENT DOCUMENTS

WO    WO 2006/107950 A2    10/2006

OTHER PUBLICATIONS

Bunz et al., *The Journal of Clinical Investigation*, 104(3), 263-269 (Aug. 1999).
DeClerck et al., *Am. J. Pathol.*, 164(4), 1131-1139 (Apr. 2004).
Dzik-Jurasz, A., "Angiogenesis Imaging In Man: A Personal View From The Pharmaceutical Industry," *The British Journal of Radiology*, Special Issue 2003, pp. S81-S82 (2003).
Encyclopaedia Britannica, "Cells: Their Structures and Functions", *The New Encyclopaedia Britannica*, V. 15, Macropaedia, 15th edition, pp. 565-593 (1994).
Farhadi, et al., "Combined Inhibition of Vascular Endothelial Growth Factor and Platelet-Derived Growth Factor Signaling: Effects on the Angiogenesis, Microcirculation, and Growth of Orthotopic Malignant Gliomas", *Journal of Neurosurgery*, 102:363-370 (Feb. 2005).
Fukuoka et al., "Multi-Institutional Randomized Phase II Trial of Gefitinib for Previously Treated Patients with Advanced Non-Small-Cell Lung Cancer", *Journal of Clinical Oncology*, vol. 21, No. 12 Jun. 15, 2003: pp. 2237-2246 DOI: 10.1200/JCO.2003.10.038.
Fuller et al., "Organelles and Vesicle Traffic," *Molecular Basis of Medical Cell Biology* (a Lange medical book), Ch. 4, pp. 67-92 (1998).
Galbraith, S.M., "Antivascular Cancer Treatments: Imaging Biomarkers in Pharmaceutical Drug Development", *The British Journal of Radiology*, 76 (2003), S83-S86 DOI: 10,1259/bjr/15255885.
Kauppinen, Risto A., "Monitoring Cytotoxic Tumour Treatment Response by Diffusion Magnetic Resonance Imaging and Proton Spectroscopy," *NMR Biomedicine*, 2002:15:6-17; DOI:10.1002/nbm.742.
Laird et al., *Cancer Research*, 2000, vol. 60, pp. 4152-4160.
Leach et al., "The Assessment of Antiangiogenic and Antivascular Therapies in Early-Stage Clinical Trials Using Magnetic Resonance Imaging; Issues and Recommendations," *British Journal of Cancer* (2005) 92 (9), pp. 1599-1610.
Mukherji et al., *AJNR Am. J. Neuroradio.*, 1996, vol. 17, pp. 1485-1490.
Nakagami et al., "Increased Choline Kinase Activity and Elevated Phosphocholine Levels in Human Colon Cancer," *Jpn. J. Cancer Res.* 90, 419-424, Apr. 1999.
Pollard, Thomas D., "Programmed Cell Death," *Cell Biology*, Elsevier, Inc., Ch. 49, pp. 767-782 (2004); ISBN 1-4160-2388-7.
Schmitt et al., *Journal of Pathology*, 187, 127-137 (1999).
Taga et al., Abstract, *International Journal of Cancer* 98(5), 690-697 (Apr. 10, 2002).
Wojtukiewicz et al., "Contribution of the Hemostatic System to Angiogenesis in Cancer", *Seminars in Thrombosis and Hemostasis*, vol. 30, No. 1 (2004) pp. 5-20.
Yamanaka et al., Abstract "Gene Therapy of Brain Tumor with Endostatin", *Drugs Today*, 40(11), 931-914 (Nov. 2004).
Daly et al., "Phospholipid Metabolism in Cancer Cells Monitored by $^{31}P$ NMR Spectroscopy," *The Journal of Biological Chemistry*, 262(31): 14875-14878 (Nov. 5, 1987).
Balkwill et al., *The Lancet*, 357, 539-545 (2001).
Bianco et al., *British Journal of Cancer*, 89, (Suppl. 2) (2003) S25-S35 Abstract.
Blackledge et al., *British Journal of Cancer*, 90, 566-572 (2004).
Bluml et al., *Magn. Reson. Med.*, 42, 643-654 (1999).
Boyer, *British Journal of Cancer*, 89, (Suppl. 2) (2003) S25-S35 Abstract.
Cappuzzo et al. *I British Journal of Cancer*, 89, (Suppl. 2) (2003) S25-S35 Abstract.
Cappuzzo et al. *II British Journal of Cancer*, 89, (Suppl. 2) (2003) S25-S35 Abstract.
Chioni et al., *British Journal of Cancer*, 89, (Suppl. 2) (2003) S25-S35 Abstract.
Colman, *Semin. Thromb. Hemost.*, 30(1), 45-61 (2004).
Cortes-Funes et al., *British Journal of Cancer*, 89, (Suppl. 2) (2003) S25-S35 Abstract.
U.S. Appl. No. 10/946,741, filed Sep. 22, 2004, Norfray.
U.S. Appl. No. 11/193,037, filed Jul. 29, 2005, Norfray.
Danielsen et al., *Magnetic Resonance Spectroscopy Diagnosis of Neurological Diseases*, Marcel Dekker, Inc. Ch. 3: The clinical significance of metabolites, 23-43 (1999).
de Braud et al., *British Journal of Cancer*, 89, (Suppl. 2) (2003) S25-S35 Abstract.
de la Cruz et al., *I British Journal of Cancer*, 89, (Suppl. 2) (2003) S25-S35 Abstract.
de la Cruz et al., *II British Journal of Cancer*, 89, (Suppl. 2) (2003) S25-S35 Abstract.
de Leeuw et al., *British Journal of Cancer*, 89, (Suppl. 2) (2003) S25-S35 Abstract.
Diaz-Canton, *British Journal of Cancer*, 89, (Suppl. 2) (2003) S25-S35 Abstract.
Dieriks et al., *British Journal of Cancer*, 89, (Suppl. 2) (2003) S25-S35 Abstract.
Eliason et al., *Current Drug Targets*, 5, 383-388 (2004).
Engelse et al., *Semin. Thromb. Hemost.*, 30(1), 71-82 (2004).
Erlich, *IDrugs*, 6(4), 331-333 (2003).
Evelhoch, *Cancer Research*, 47, 3396-3401 (Jul. 1, 1987).
Fernandez et al., *Semin. Thromb. Hemost.*, 30(1), 31-44 (2004).
Fisher et al., *Neuroimg. Clin. N. Am.* 12, 477-499 (2002).
Fujimoto et al., *The 11th International Congress of Immunology* (2001) (Abstract).
Fulham et al., *Radiology*, 185, 675-686 (1992).
Gelibter et al., *British Journal of Cancer*, 89, (Suppl. 2) (2003) S25-S35 Abstract.
Gervais et al., *British Journal of Cancer*, 89, (Suppl. 2) (2003) S25-S35 Abstract.
Griffiths et al. *The Lancet*, 1435-1436, (Jun. 25, 1983).
Harrigan, *Neurosurgery*, 53(3), 639-660 (2003).
Jin et al., *Br. J. Cancer*, 90, 561-565 (2004).
Katz et al., *British Journal of Cancer*, 89 (Suppl. 2) (2003) S25-S35 Abstract.
Kowalski et al., *British Journal of Cancer*, 89, (Suppl. 2) (2003) S25-S35 Abstract.
Kreis et al., *J. Magnetic Resonance Series B*, 102, 9-19 (1993).
Lynch et al., *New England Journal of Medicine*, 350(21), 2129-2139 (May 20, 2004).
Maione et al., *British Journal of Cancer*, 89, (Suppl. 2) (2003) S25-S35 Abstract.
Mancuso et al., *British Journal of Cancer*, 89, (Suppl. 2) (2003) S25-S35 Abstract.
Martin-Algarra et al., *British Journal of Cancer*, 89, (Suppl. 2) (2003) S25-S35 Abstract.
Martinez, *British Journal of Cancer*, 89, (Suppl. 2) (2003) S25-S35 Abstract.
Matsumoto et al., *Jpn. J. Clin. Oncol*, 34(3), 124-130 (2004).
Negendank, *NMR In Biomedicine*, 5, 303-324 (1992).
Negendank, *Radiology*, 185, 875-883 (1992).
Nie et al., *Semin, Thromb. Hemost.* 30(1), 119-125 (2004).
Norfray et al., *AJR*, 173, 119-125, (Jul. 1999).
Norfray et al., *AJR*, 182(3), 3-13, (Jan. 2004).
Norfray et al., *Journal of Computer Assisted Tomography*, 23(6), 994-1003 (1999).
Norfray, et al., *Pediatric Neurosurgery*, 4th Edition, Ch. 110, McLone (ed), 1189-1203 W.B. Sunders Co. (2001).
Norfray et al., *ARRS Annual Meeting*, (May 4-9, 2003) 1 page Abstract.
Petersen et al., *British Journal of Cancer*, 89, (Suppl. 2) (2003) S25-S35 Abstract.
Petruzelka et al. *British Journal of Cancer*, 89, (Suppl. 2) (2003) S25-S35 Abstract.
Podo, *NMR in Biomedicine*, 12, 413-429 (1999).
Ranson et al., *Journal of Clinical Oncology*, 20(9), 2240-2250 (May 1, 2002).
Razis et al., *British Journal of Cancer*, 89, (Suppl. 2) (2003) S25-S35 Abstract.
Reck et al., *British Journal of Cancer*, 89, (Suppl. 2) (2003) S25-S35 Abstract.
Ross et al. *Arch. Surg.*, 122, 1464-1469 (Dec. 1987).

Ross, *The Biochemistry of Living Tissues: Examination by MRS*, 215-219 (1992).

Ross et al., *Magnetic Resonance Quarterly*, 10, 191-247 (1994).

Ross et al., *Journal of Computer Assisted Tomography*, 13(2), 189-193, (Mar./Apr. 1989).

Ross et al., *The Lancet*, 641-646 (Mar. 1984).

Ruiz-Cabello, *NMR in Biomedicine*, 5, 226-233 (1992).

Schwarz et al., *The British Journal of Radiology*, 75, 959-966 (Dec. 2002).

Sierko et al., *Semin. Thromb. Hemost.*, 30(1), 95-108 (2004).

Stein et al., *British Journal of Cancer*, 89, (Suppl. 2) (2003) S25-S35 Abstract.

Tang et al., *Semin. Thromb. Hemost.* 30, 109-117 (2004).

van der Kamp et al., *British Journal of Cancer*, 89, (Suppl. 2) (2003) S25-S35 Abstract.

van Zandwijk, *I British Journal of Cancer*, 89, (Suppl. 2) (2003) S25-S35 Abstract.

van Zandwijk, *II British Journal of Cancer*, 89, (Suppl. 2) (2003) S25-S35 Abstract.

Vincent, *British Journal of Cancer*, 89, (Suppl. 2) (2003) S25-S35 Abstract.

Wojtukiewicz et al., *Semin. Thromb. Hemost.* 30(1), 145-156 (2004).

Yu et al., *Semin. Thromb. Hemost.* 30(1), 21-30 (2004).

Bernales et al., Autophagy counterbalances endoplasmic reticulum expansion during the unfolded protein response, *PLoS Biology*, 4 (12): (e423) 2311-2324 (Dec. 2006).

Blankenberg et al., Detection of apoptotic cell death by proton nuclear magnetic resonance spectroscopy, *Blood*, 87: 1951-1956 (1996).

Blankenberg et al., Quantitative analysis of apoptotic cell death using proton nuclear magnetic resonance spectroscopy, *Blood*, 89 (10): 3778-3786 (May 15, 1997).

Bursch et al., Programmed cell death (PCD): apoptosis, autophagic PCD, or others?, *Annals N.Y. Academy of Science*, 926: 1-13 (Dec. 2000).

Clemens et al., Translation initiation factor modifications and the regulation of protein synthesis in apoptotic cells, *Cell Death and Differentiation*, 7:603-615 (2000).

European Patent Office, Supplementary European search report for cognate European Application No. 06733897.0, mailed Feb. 20, 2009.

European Patent Office, Communication pursuant to Article 94(3) EPC relating to cognate European Application No. 06733897.0, mailed Jun. 18, 2009.

Ferreira et al., Apoptosis: target of cancer therapy, *Clinical Cancer Research*, 8: 2024-2034 (Jul. 2002).

Lindskog et al., Predicting resistance or response to chemotherapy by proton magnetic resonance spectroscopy in neuroblastoma, *Journal of the National Cancer Institute*, 96 (19): 1457-1466 (2004).

Maiuri et al., Self-eating and self-killing: crosstalk between autophagy and apoptosis, *Nature Reviews/Molecular Cell Biology*, 8: 741-752 (Sep. 2007).

Meisamy et al., Neoadjuvant chemotherapy of locally advanced breast cancer: predicting response with in vivo $^1$H MR spectroscopy—a pilot study at 4 T$^1$, *Radiology*, 233: 424-431 (2004).

Mohamad et al., Mitochondrial apoptotic pathways, *Biocell*, 29(2): 149-161 (2005).

Schmitt et al., Apoptosis and therapy, *Journal of Pathology*, 187:127-137 (1999).

Scott et al., $^{13}$C-NMR investigation of protein synthesis during apoptosis in human leukemic cell lines, *Journal of Cellular Physiology*, 181: 147-152 (1999).

Shaffer et al., XBP1, downstream of blimp-1, expands the secretory apparatus and other organelles, and increases protein synthesis in plasma cell differentiation, *Immunity*, 21: 81-93 (Jul. 2004).

\* cited by examiner

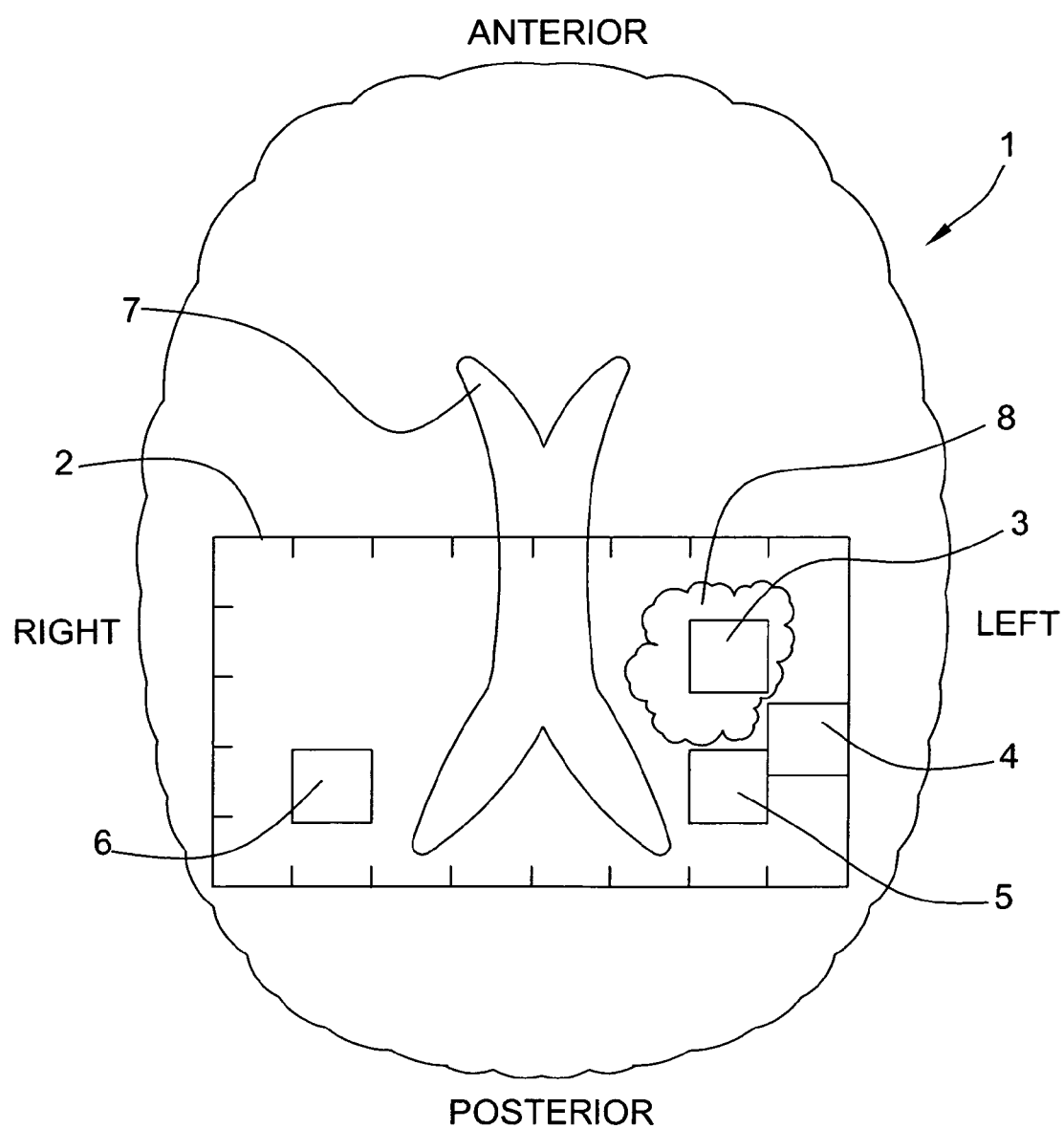

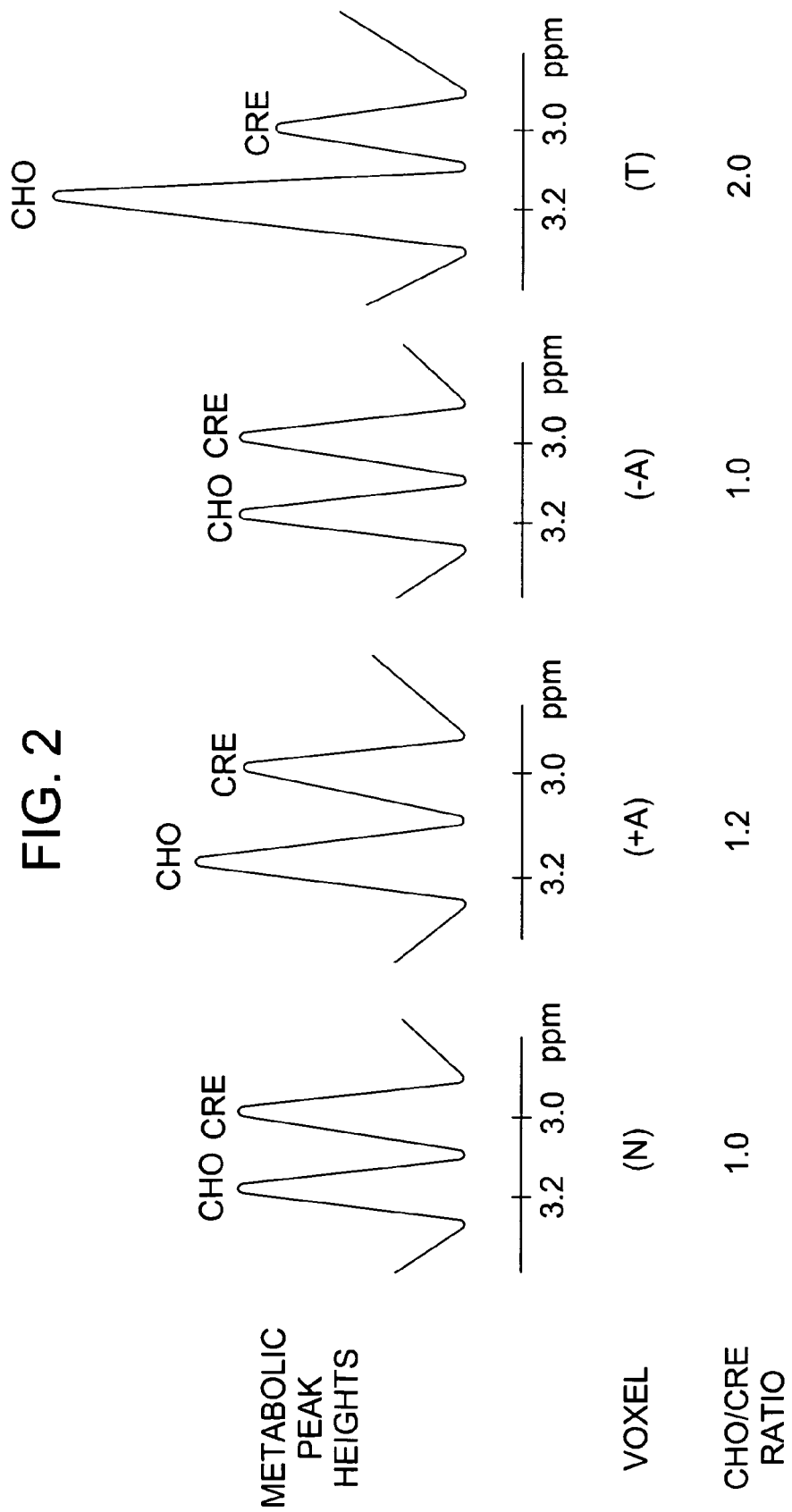

METHOD FOR MONITORING EARLY TREATMENT RESPONSE

FIELD OF THE INVENTION

This invention pertains to a method for monitoring early response to a treatment of a disease in general, and cancer in particular, for example, a cancer treatment involving the use of an angiogenesis inhibitor. The method employs Magnetic Resonance Spectroscopy (MRS).

BACKGROUND OF THE INVENTION

There is a need for monitoring the effectiveness of a disease treatment, particularly for diseases where the condition of the patient can deteriorate rapidly if the treatment is not effective. One such disease is cancer, particularly, metastasis of cancer, which involves angiogenesis. Angiogenesis, which is formation of new blood vessels from preexisting ones, is known to be important for tumor growth and metastasis. Without blood supply, tumor growth is diffusion-limited, and is generally restricted to less than 1 mm$^3$ to 2 mm$^3$. The recruitment of a vascular supply allows a tumor to grow beyond this limited volume and provides a route for metastasis. Angiogenesis supplies oxygen and nutriments needed for tumor growth.

Typically, the angiogenesis process takes place as follows. The diseased tissue produces and releases angiogenic growth factors (proteins) that diffuse into the nearby tissues. The angiogenic growth factors bind to specific receptors located on the endothelial cells of nearby preexisting blood vessels. Once growth factors bind to their receptors, the endothelial cells become activated. Signals are sent from the cell's surface to the nucleus. The endothelial cell's machinery begins to produce new molecules including enzymes. Enzymes form tiny openings in the sheath-like covering (basement membrane) surrounding all existing blood vessels. The endothelial cells begin to divide (proliferate), and they migrate out through the openings of the existing vessel towards the diseased tissue (tumor). Specialized molecules called adhesion molecules, or integrins ($\alpha_v\beta_3$, $\alpha_v\beta_5$), serve as grappling hooks to help pull the sprouting new blood vessel sprout forward. Additional enzymes (matrix metalloproteinases or MMP) are produced to dissolve the tissue in front of the sprouting vessel tip in order to accommodate it. As the vessel extends, the tissue is remolded around the vessel. Sprouting endothelial cells roll up to form a blood vessel tube. Individual blood vessel tubes connect to form blood vessel loops that can circulate blood. The newly formed blood vessel tubes are stabilized by specialized muscle cells (smooth muscle cells, pericytes) that provide structural support. Blood flow begins.

In angiogenesis, the neoplastic cells can recruit, in addition to normal endothelial cells, the macrophages, fibroblasts, mast cells, and/or platelets to generate new vessels from pre-existing ones at the periphery of the tumor. Angiogenesis is thus orchestrated by a web of signaling pathways controlled by proangiogenic protein signaling molecules. The proangiogenic signaling molecules arise from the tumor and react with the cells in the surrounding normal tissue (paracrine molecules). The proangiogenic signaling molecules are generated from cells in the normal surrounding tissue reacting with adjacent, non-neoplastic cells, and reacting with matrix of the tissue (juxtacrine molecules). Proangiogenic signaling proteins are generated from a cell in the tissue that reacts with itself (autocrine molecules). Fisher, M. J., et al., *Neuroimg. Clin. N. Am.* 12, 477-499 (2002), and Ch. 9 in *Molecular Basis of Medical Cell Biology*, 1st ed., Fuller, G. M., et al. (Eds.) Appleton and Large (1998).

Some of the common approaches to cancer treatment (including metastasis of cancer) involve surgery, radiation therapy, and/or chemotherapy. Radiation therapy and chemotherapy are effective if they are capable of killing the tumor cells; i.e., when they act as cytotoxic agents. Typically, the response to radiation therapy or chemotherapy is monitored by magnetic resonance imaging (MRI) of the tumor, wherein a decrease in tumor size is indicative of positive response to treatment.

Angiogenesis inhibitors have been proposed for cancer treatment. For example, interrupting the signaling proangiogenic pathways interrupts the blood supply to the tumor, and thereby, stops neoplastic proliferation. The major proangiogenic signaling pathways involve growth factors, integrins/proteases, coagulation/fibrinolysis factors and inflammatory factors.

The angiogenesis inhibitors are cytostatic rather than cytotoxic; accordingly, classical signs of treatment response, e.g., decreased tumor size or decreased enhancement, commonly observed in treatments involving cytotoxic agents, may not be observed with cytostatic angiogenesis inhibitors. Accordingly, classical imaging techniques such as MRI alone may not be suitable or adequate to monitor response to a treatment involving angiogenic inhibitors.

Magnetic Resonance Spectroscopy or MRS has been proposed as a tool for obtaining information on cellular metabolism; see, for example, Norfray, J. et al., Ch. 110 in *Pediatric Neurosurgery*, 4$^{th}$ ed., McLone, D. G., et al. (Eds), W.B. Saunders Co. (2001). MRS also has been proposed for diagnosing the treatment response of tumors with cytotoxic agents; see, for example, Fulham, M. J., et al., *Radiology*, 185, 675-686 (1992), which discloses that brain tumor metabolism was studied with $^1$H MRS before and after treatment with radiation therapy. MRS permits non-invasive examination of metabolic characteristics of human cancers in a clinical environment. Accessible nuclei include $^{31}$P, $^{13}$C, $^1$H, and $^{23}$Na. $^{31}$P MRS contains information about energy status (phosphocreatine, inorganic phosphate, and nucleoside triphosphates), phospholipids metabolites (phosphomonoesters and phosphodiesters), intracellular pH (pH NMR), and free cellular magnesium concentration ($Mg^{2+}$ f). Water-suppressed $^1$H MRS shows total choline, total creatine, lipids, glutamate, inositols, lactate, and the like. Negendank, W., *NMR in Biomedicine*, 5, 303-324 (1992).

Further, U.S. Pat. No. 6,681,132 (Katz et al.) discloses a method for determining the effectiveness of chemotherapy comprising administering a dose of a cytotoxic antineoplastic agent to a subject prior to surgical removal of a cancerous tumor, acquiring magnetic resonance data from the subject, and determining whether the treatment has affected the population of a nucleus or nuclei, particularly $^{23}$Na. Negendank, W., supra, provides a review of various studies of human tumors by MRS.

In addition, Ross, B. et al., *The Lancet*, 641-646 (1984) discloses monitoring response to cytotoxic chemotherapy of intact human tumors by $^{31}$P MRS; Griffiths, J. R. et al., *The Lancet*, 1435-36 (1983) discloses the use of $^{31}$P MRS to follow the progress of a human tumor during chemotherapy with doxorubicin; Ross, B. et al., *Arch. Surg.*, 122, 1464-69 (1987) discloses the monitoring of chemotherapeutic treatment response of osteosarcoma and other neoplasms of the bone by $^{31}$P MRS; and Norfray, J. F. et al., *J. Computer Assisted Tomography*, 23(6), 994-1003 (1999) discloses an MRS study of the neurofibromatosis type 1 intracranial lesions.

While MRS is effective as a tool for monitoring treatment response, the disclosures in the art show that it has been applied to monitor the response to cytotoxic agents (radiation and chemotherapy). In many cases, a detectable change in tumor size is observed only after a significantly long period of time, for example, after treatment for a period of about 3 months or more. Such long periods of time could be harmful to the patient, especially if the treatment has not been effective or only partially effective, such as, for example, treatments involving the use of angiogenesis inhibitors; during this long period of time, tumor cells could multiply or metastasize, and lead to worsening of the patient's condition.

The foregoing shows that there exists a need for a method where an early treatment response can be monitored in diseases, especially where the treatment involves the use of one or more angiogenesis inhibitors. Accordingly, the present invention provides such a method. This and other advantages of the invention, as well as additional inventive features, will be apparent from the description of the invention provided herein.

BRIEF SUMMARY OF THE INVENTION

The invention provides a method for monitoring early treatment response of a disease treatment, particularly cancer treatment, comprising measuring by MRS, the amount of Choline, e.g., total choline, present in a tissue adjoining or surrounding the diseased or cancerous tissue before and after treatment. The treatment, in one aspect, comprises administration of an angiogenesis inhibitor, whereby a decrease in the amount of Choline after treatment is indicative of a positive response. In accordance with the invention, the tissue surrounding the tumor can be monitored by following cell membrane metabolism utilizing the Choline peak on $^1$H MR spectroscopy. The Choline peak represents the visible mobile Choline forming the plasma and organelle cell membranes. A decrease in the Choline identifies treatment response; an increase in the Choline peak identifies treatment failure.

The present invention also provides a method for monitoring early treatment response of an angiogenesis effector, i.e., an inhibitor or promoter of angiogenesis, treatment in a diseased animal comprising measuring, by Magnetic Resonance Spectroscopy (MRS), the amount of Choline present in the diseased tissue before and after treatment, wherein said treatment comprises administration of an angiogenesis effector, whereby a change in the amount of Choline after treatment is indicative of a response.

The present invention provides one or more advantages, for example, changes in the amount of Choline occurring immediately following a treatment can be detected by the method of the present invention even before the amount of change required for determination by classical methods such as MRI imaging occurs in the tissue. When MRS is used in conjunction with MRI, in accordance with an embodiment of the invention, the present invention offers the combined advantages of MRI and MRS and provides a method to monitor early treatment response. The present invention also provides a method for monitoring cancer treatment, especially a treatment of cancer susceptible to metastasize.

BRIEF DESCRIPTION OF THE DRAWINGS

FIG. 1 schematically depicts an axial view of a human brain 1. A region of interest (ROI) is depicted as rectangle 2 comprising the tumor 8. Voxels 3-6 are the areas for determining the amounts of Choline in the cell membranes. 3 is V(T), a voxel located within the tumor. 4 is V(−A), a voxel where angiogenesis does not take place. 5 is V(+A), a voxel where angiogenesis takes place. 6 is V(N), a voxel in the normal tissue. 7 depicts lateral ventricles.

FIG. 2 depicts an illustration of $^1$H MRS peaks corresponding to Choline (CHO) and creatine (CRE) in voxels V(N), V(+A), V(−A) and V(T). The X-axis represents chemical shift in parts per million (ppm) and the Y-axis represents peak intensities of the metabolites in arbitrary units. The CHO/CRE ratio is illustrated for each voxel.

DETAILED DESCRIPTION OF THE INVENTION

The present invention is predicated on monitoring changes in the amount of one or more metabolites occurring in an internal cell membrane, for example, changes induced by the down-regulation of one or more of the intracellular organelles and their secretory granules and transport vesicles. The internal cell membranes constitute nearly 90% of the total cell membranes, and form the membranes of the nucleus, the mitochondria, the lysosomes, the peroxisomes, the endoplasmic reticulums, the Golgi apparatus, the secretory granules, and the transport vesicles. The angiogenesis inhibitors down-regulate the intracellular organelles and their secretory granules and transport vesicles of cells recruited by the tumor at its periphery.

Accordingly, the present invention provides, in an embodiment, a method for monitoring early treatment response of a cancer treatment comprising measuring, by Magnetic Resonance Spectroscopy (MRS), the amount of Choline present in a tissue adjoining or surrounding the cancerous tissue before and after treatment; the treatment comprises administration of an angiogenesis inhibitor, whereby a decrease in the amount of Choline after treatment is indicative of a positive response. MRS can be based on the resonance of any suitable nuclei; for example, nuclei selected from the group consisting of $^{31}$P, $^1$H, $^{13}$C, and $^{23}$Na, and any combination thereof; preferably, $^1$H.

The term "Choline" herein is used to denote choline (($CH_3$)$_3$N$^+$CH$_2$CH$_2$OH), a derivative of choline, or a combination of choline and/or one or more derivatives of choline. Examples of choline derivatives include lysophosphatidylcholine, or glycerophosphocholine, phosphomonoesters of choline (e.g., phosphocholine), phosphodiesters of choline (e.g., phosphatidylcholine), sphingomyelin, phosphoethanolamine, glycerophosphoethanolamine, or any combination thereof. In an embodiment of the invention, the term "Choline" represents the sum of choline and all choline derivatives (or total choline), for example, the sum of choline and phosphocholine. Phosphoserine and glycerophosphoserine also can be monitored Ruiz-Cabello, J. et al., *NMR in Biomedicine,* 5, 223-233 (1992); Podo, F., *NMR in Biomedicine,* 12, 413-439 (1999); and Blüms, S. et al., *Magn. Reson. Med.,* 42, 643-654 (1999).

A decrease in the amount of Choline occurs very early in the surrounding cells recruited by the tumor as a result of the down-regulation. Since choline contains 9 protons per molecule (as trimethylamines or trimethylammonium salts), the Choline signal is amplified nine-fold. Since up to 90% of the cell membranes can be down-regulated in recruited cells, MRS provides a sensitive method to monitor early treatment response.

The amount of Choline can be measured by MRS in any suitable manner. For example, the amount of Choline can be measured by measuring the height of a peak or peaks corresponding to Choline. In another embodiment, the amount of Choline can be measured by measuring the area under a peak or peaks corresponding to Choline. In yet another embodiment, the amount of Choline can be measured by measuring the ratio of the height of a peak or peaks corresponding to Choline relative to the height of a peak or peaks of an internal standard. In a further embodiment, the amount of Choline can be measured by measuring the ratio of the area under a peak or peaks corresponding to Choline relative to the area under a peak or peaks of an internal standard.

Any suitable internal standard can be used. For example, the internal standard can be total creatine when the MRS is based on $^1$H resonance, or internal standard can be adenosine triphosphate (ATP) when the MRS is based on $^{31}$P resonance. The term "total creatine" refers to the combination of creatine and phosphocreatine. Creatine is buffered in cell systems; accordingly, the amount of creatine remains substantially constant.

It is contemplated that the method of the present invention is applicable to monitoring early treatment response wherein the treatment involves inhibition of angiogenesis by interrupting one or more of the proangiogenic pathways involving growth factors, integrins/proteases, coagulation/fibrinolytic factors, and/or inflammatory factors. In accordance with an embodiment, the invention provides a method for monitoring early treatment response of a treatment involving the use of an angiogenesis inhibitor, wherein the angiogenesis inhibitor interrupts a proangiogenic pathway, e.g., one or more pathways selected from the group consisting of a growth factor signaling pathway, an integrin/protease pathway, a coagulation/fibrinolysis pathway, and an inflammatory signaling pathway, and any combination thereof.

Angiogenesis can involve one or more of a number of signaling pathways. Angiogenesis is initiated by hypoxia, mutant oncogenes and/or tumor suppressor genes that turn on the signaling pathways utilizing signaling proteins. Intracellular organelles are up-regulated to generate the increase in signaling proteins.

In the growth factors signaling pathway, malignant cells secrete angiogenic growth factors in response to hypoxia, mutated oncogenes, and/or tumor suppressor genes. The proangiogenic growth factors secreted by the tumor react with the normal surrounding cells. Vascular endothelial growth factor (VEGF) plays a role in this signaling pathway by binding to endothelial cells (EC) and causing their proliferation, increase survival and vascular permeability. Tumor VEGF expression is further stimulated by various tumor cytokines and growth factors including basic fibroblastic growth factor (bFGF), platelet derived growth factor (PDGF), insulin-like growth factor (IGF-1), tumor necrosis factors (TNF-α and TNF-β), angiopoietin-2, as well as hypoxia-inducible factor-1 (HIF-1). Fisher, et al., supra and Tang, D. G., et al., Semin. Thromb. Hemost. 30, 109-117 (2004). The recruited endothelial cells, fibroblasts, and platelets, in turn, generate growth factors further promoting angiogenesis.

In the integrin/protease signaling pathway, endothelial cells utilize the surface $\alpha_3B_1$, integrin receptor to adhere with urokinase-type plasminogen activator (U-PA) in the extracellular matrix (ECM) to form plasmin, a serine protease. Plasmin dissolves the ECM allowing EC to tunnel into the ECM. DeClerck, Y. A., et al., Am. J. Pathol. 161, 1131-1139 (2004). Endothelial cells also utilize the surface $\alpha_vB_3$ integrin receptor to activate matrix metalloproteinases (MMP) in the ECM allowing the new vessels to grow towards the tumor. Engelse, M. A., et al., Semin. Thromb. Hemost. 30, 71-82 (2004). During angiogenesis the integrin surface receptors of EC are increased in number by the EC transcription factors that are stimulated by tumor VEGF. DeClerck et al., supra.

In the coagulation/fibrinolysis signaling pathway, the tissue factor (TF), which is a glycoprotein surface receptor, is the initiator of the signaling pathway. Usually TF is quiescent, being sequestered on cells within the subendothelium of vessel walls. The release of tumor VEGF causes fenestration of the endothelial layer thereby increasing vascular permeability and exposing TF. TF comes in contact with circulating factor (F) VII that escapes into the ECM because of vascular permeability. The TF/F VII combination initiates the coagulation cascade by activating thrombin in the ECM. Thrombin has many proangiogenic effects including increasing VEGF receptors (VEGFR) on EC, releasing VEGF from platelets, releasing bFGF from ECM and EC, and releasing tissue type plasminogen (tPA) from EC thereby activating MMP to dissolve the ECM. The final step of the coagulation cascade is cleavage of plasma fibrinogen (FBG) to fibrin by thrombin. Fibrinogen is a plasma protein of hepatic origin that escapes into the ECM because of vascular permeability. Proteolytic breakdown of FBG by thrombin releases fibrin. Cross-linked fibrin supports EC adhesion, migration and survival by degrading bFGF and release of interleukin 8. Fernandez, P. M., et al., Semin. Thromb. Hemost. 30, 31-44 (2004). Platelets amplify the coagulation reaction by entering the ECM. The platelets form aggregations and become activated by collagen, thrombin, and fibrinogen in the ECM. The activated platelets release their secretory granules containing VEGF, bFGF, IGF-1, PDGF, and Ang-1, as well as other proangiogenic factors. Sierko, E., et al., Semin. Thromb. Hemost. 30, 95-108 (2004).

In the inflammatory signaling pathway, inflammatory cells escape into the ECM because of vascular permeability. The inflammatory cells adhere to the platelet aggregations in the ECM. The inflammatory cells and platelets release additional VEGF, as well as, other cytokines that stimulate angiogenesis, including the arachidonic acid metabolism by cyclooxygenase (COX) and lipoxygenase (LOX) to form prostaglandins and leukotrienes. Nie, D. et al., Semin. Thromb. Hemost. 30, 119-125 (2004). The neoplastic cells also release tumor necrosis factor (TNF), interleukin-1 (IL-1), interleukin-6 (IL-6), and monocytic chemotactic protein-1, mediating inflammation by attracting macrophages, neutrophils, fibroblasts, and mast cells. The inflammatory cells release cytokines and chemokines that contribute to angiogenesis. Balkwill, F., et al., Lancet 357, 539-545 (2001).

In accordance with an embodiment of the invention, the angiogenesis inhibitor can cause an interruption in an up-regulated intracellular organelle; for example, an interruption of the production of the secretory granules and/or the transporting vesicles. In accordance with another embodiment of the invention, the angiogenesis inhibitor can cause an interruption in the function of the Golgi apparatus. In further embodiments of the invention, the angiogenesis inhibitor can cause an interruption in the function of the lysosomes, the endoplasmic reticulum, the mitochondrion, the nucleus, and/or the peroxisomes.

Angiogenesis inhibitors can interrupt the proangiogenic signaling pathways, for example, the growth factor signaling pathway. Production of growth factors is interrupted by blocking the growth factor cell surface receptor with tyrosine kinase inhibitors (TKI) or with monoclonal antibodies. Blackledge, G. et al., Br. J. Cancer 90, 566-572 (2004). Examples of VEGF receptor (VEGFR) TKI include SU5416 and SU6668, the latter also inhibiting bFGF and PDGF receptors. Fisher et al., supra. Monoclonal antibodies to growth factor receptors also inhibit angiogenesis and include, cetuximab, IMC-C225, ABX-EGF, HuMax-EGFR, and a monoclonal antibody to VEGFR (DC101); Fisher et al., supra, and Blackledge et al., supra, as well as other monoclonal antibodies such as gefitinib, erlotinib, canertinib, EKB-569, and lapatinib. Other agents to block VEGF signaling include VEGF toxin conjugates, dominant negative VEGF-2, soluble VEGFR (VEGF-TRAP) and antisense oligonucleotides. Suramin, an antiparasitic agent has antiangiogenic effects by inhibiting both VEGF and bFGF. Fisher et al., supra. Growth factors are also inhibited by antagonists of transforming kinases (gleevec, herceptin), farnesyl transferase inhibitors, and agents targeting tumor suppressors, such as p53 (PRIMA-1). Yu, J. L. et al., Semin. Thromb. Hemost. 30, 21-30 (2004). Examples of angiogenesis inhibitors that inhibit VEGF proliferation of endothelial cells include thalidomide and squalamine. Thalidomide inhibits the processing of messenger RNA (mRNA) for VEGF thereby producing an antiangiogenic effect. Balkwill, F., et al., supra. Squalamine inhibits the VEGF effect by changing the shape of the endothelial cell. Fisher et al., supra.

The angiogenesis inhibitors can inhibit the integrin/protease signaling pathway. The integrin-mediated cell adhesion is interrupted by antibody and peptide integrin inhibitors, thereby inhibiting angiogenesis. Anti-$\alpha_v B_3$ integrin antibody (Vitaxin), anti-$\alpha_v B_1$, integrin antibody, and a cyclic peptide inhibitor of integrin $\alpha_v B_3 // \alpha_v B_5$ (Cilengitide) are in clinical trials. Jin, H. et al., Br. J. Cancer 90, 561-565 (2004). An inhibitor (TNP-470) to urokinase-type plasminogen activator (U-PA) prevents the EC surface $\alpha_3 B_1$, integrin to adhere, thereby preventing the formation of plasmin. Fisher et al., supra. Inhibitors to plasmin, such as $\alpha$2-antiplasmin and $\alpha$2-macroglobulin, have antiangiogenic activity. Antiangiogenic activity occurs when kininostatin binds to U-PA receptor (U-PAR), thereby initiating apoptosis. Colman, R. W., Semin. Thromb. Hemost. 30, 45-61 (2004). Inhibition of matrix metalloproteinases (MPs) occurs by normal tissue inhibitors of MPs (TIMPs). MMP can also be inhibited by $\alpha$2-macroglobulins. Examples of MMP inhibitors include, BMS275291, COL-3, marimastat, neovastat, and solimastat. Engelse et al., supra and Fisher et al., supra. Angiogenesis inhibitors can be derived from proteolytic cleavage of the basement membrane or from proteolytic cascades. Angiostatin is produced by hydrolysis of plasminogen by MMPs, elastases, and U-PA-activated plasmin and causes endothelial apoptosis. Endostatin is the C-terminal fragment of collagen XVIII and inhibits VEGF induced migration of EC, and binds to EC integrins also impairing EC migration. Engelse et al., Semin. Thromb. Hemost. 30, 71-82 (2004).

The angiogenesis inhibitors can inhibit the coagulation/fibrinolytic signaling pathway. The coagulation/fibrinolytic signaling pathway in normal subjects is quiescent being modulated by proangiogenic and antiangiogenic factors. Several antiangiogenic factors are released during wound healing, and are now being investigated in the treatment of cancer. During the proteolysis of prothrombin, cryptic kringle fragments are released inhibiting angiogenesis. Antithrombin (AT) fragments are generated during the proteolytic breakdown of thrombin, blocking TF and VEGF. Fibrinogen-E and fibrin-D fragments both have antiangiogenic effects. Platelets release thrombospondin-1 and platelet factor-4 (PF-4) both with antiangiogenic effects. The coagulation/fibrinolytic signaling pathway can be blocked with low molecular weight heparins (LMWH) by competing with growth factors for binding sites in the ECM. Wojtukiewicz, M. S., et al., Semin. Thromb. Hemost. 30, 145-156 (2004).

The angiogenesis inhibitors can inhibit the inflammatory signaling pathway. Inhibitors to the mobilization of arachidonic acid prevent the release of angiogenic products including prostaglandin H2 (PGH2) and hydroxyeicosatetraenoic acids (HETEs). Cyclooxygenase (COX) inhibitors and lipoxygenase (LOX) inhibitors prevent the release of the proangiogenic factors, thereby, blocking the inflammatory signaling pathway and angiogenesis. Nie et al., supra. Examples of COX inhibitors include Vioxx and Celebrex. Balkwill, F., et al., supra. Other angiogenesis inhibitors in the inflammatory process include interferon-$\alpha$ and $\beta$ that downregulate bFGF expression and inhibits its mitogenic effects. Fisher, et al., supra. Two TNF antagonists (etanercept and infliximab) have been shown to reduce angiogenesis, prevent leukocytic infiltration and inhibit MMP. Balkwill, F., et al., supra.

The present invention provides, in an embodiment, a method for monitoring early treatment response as described above, wherein the angiogenesis inhibitor is selected from the group consisting of VEGF receptor tyrosine kinase inhibitors, monoclonal antibodies to growth factor receptors, VEGF toxin conjugate, dominant negative VEGF-2, soluble VEGFR (VEGF-TRAP) and antisense oligonucleotides, growth factor transforming kinases, farnesyl transferase inhibitors, agents targeting tumor suppressors, agents that inhibit proliferation of endothelial cells, antibody and peptide integrin inhibitors, plasmin inhibitors, urokinase-type plasminogen activator inhibitors, matrix metalloproteinase inhibitors, cyclooxygenase inhibitors, lipoxygenase inhibitors, and inhibitors of mitogenic effects, and any combination thereof.

The present invention provides a method for monitoring early treatment response, wherein the angiogenesis inhibitor is selected from the group consisting of SU5416, SU6668, cetuximab, gefitinib, erlotinib, canertinib, EKB-569, lapatinib, IMC-C225, ABX-EGF, HuMax-EGFR, DC101, suramin, gleevec, herceptin, p-53 (PRIMA-1), thalidomide, squalamine, anti-$\alpha_v B_3$ integrin antibody, anti-$\alpha_v B_5$ integrin antibody, cyclic peptide inhibitor of integrin $\alpha_v B_3 // \alpha_v B_5$, cilengitide, fumagallin, TNP-470, EMD 121974, $\alpha$2-antiplasmin, $\alpha$2-macroglobulin, kininostatin, BMS275291, COL-3, marimastat, neovastat, solimastat, angiostatin, endostatin, antithrombin fragments, fibrinogen-E, fibrin-D, thrombospondin-1, platelet factor-4, low molecular weight heparins, Vioxx, Celebrex, interferon-$\alpha$ and $\beta$, and any combination thereof.

MRS is important for evaluating treatment response to cytostatic inhibitors because of the unique information gained. During a single MRS acquisition unique information is gained from the tumor bed and the surrounding tissue. MRS monitors changes in protein metabolism by observing the changes in the intracellular membranes of organelles that generate and transport the signaling proteins to the plasma membrane. The changes in the total choline occur before the classical imaging findings of changes in size and enhancement. Since MRS is a non-invasive study, sequential studies can be performed with different inhibitor dose schedules, as well as, with combinations of chemotherapy. Since a web of signaling pathways support tumor growth and angiogenesis, a decrease in choline, e.g., total choline, confirms an appropriate inhibitor to tumor growth and angiogenesis.

MRS is important for evaluating treatment response because of the availability of the method. MRS is available commercially on magnetic resonance units to study human subjects, animals and cultured, perfused cellular extracts. MRS can quantify changes in choline, and utilizing similar pulse sequences, results can be statistically analyzed from worldwide sites during drug trials In accordance with the present invention, any suitable cancer or tumor can be treated, for example, a cancer selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, gastric cancer, pancreatic cancer, neuroblastoma, mesothelioma, prostate cancer, bone cancer, kidney cancer, and hepatocellular cancer.

In accordance with the present inventive method, early treatment response can be measured within a period of about 168 hours, preferably about 24 hours, and more preferably about 12 hours, of the treatment. For example, the response can be monitored every 12, 24, 36, 48, 60, 72, 84, 96, 108, 120, 132, 144, 156, or 168 hours, or any combination thereof, after administration of the angiogenesis inhibitor.

The present invention also provides a method for monitoring cancer treatment comprising: (a) localizing a tumor in a patient; (b) selecting a region of interest (ROI) of the tumor and a tissue adjoining or surrounding the tumor; (c) obtaining magnetic resonance spectra (MRS) of the ROI; (d) measuring the amount of Choline, e.g., total choline, from the MRS spectra; (e) initiating treatment comprising administering an angiogenesis inhibitor; (f) obtaining MR spectra of the tumor at the same ROI within a period of 7 days, preferably 3 days, and more preferably within 1 day, of initiating treatment; (g) measuring the amount of Choline from the MR spectra; and (h) comparing the amount of Choline obtained before treatment with the amount of Choline obtained after treatment; whereby a decrease in the amount of Choline after treatment is indicative of a positive response to treatment.

The basis for clinical MR studies (e.g., MRS or MRI) is the one of the nuclei, for example, the hydrogen nucleus—the proton. The same machinery is used for these studies. They differ in the software manipulation of the emitted radiofrequency (RF) from the $^1H$ nuclei. In MRI, the signal is used to create the image; in MRS, the signal is used to create the spectrum. Fourier Transform principle is the basis of the computer that allows the MRS software to separate the individual RFs within the signal. The spectrum therefore represents the different RFs being emitted within the selected region of interest (ROI). The points along the horizontal axis of the spectrum represent specific RFs emitted from each metabolite. The vertical axis of the spectrum is proportional to the amount of each metabolite forming the area beneath the RF peaks. Spectra can be obtained on 0.5 to 2.0 T MR scanners, although high-field strength scanners provide better definition of the spectra. Spectra obtained with different-strength scanners can be compared on a scale in parts per million (ppm) along the horizontal axis because metabolites always reside at one or more specific sites, for example, alanine resides at 1.47, N-acetylaspartate resides at 2.0 and 2.6 ppm, creatine resides at 3.0 and 3.9 ppm, Choline resides at 3.2 ppm, and water resides at 5.0 ppm.

Any suitable MR spectrometer can be used in the practice of the present invention. Clinical MR spectra can be obtained on MR scanners, for example, utilizing the clinical spectroscopy package called proton brain exam/single voxel (PROBE/SV) developed by General Electric Medical Systems (Milwaukee, Wis.) for use with GE's 1.5 Tesla (T) MR scanner. See Norfray, J. et al., supra, and Norfray, J. F. et al., supra, for procedures for obtaining MR spectra, identification of the peaks corresponding to metabolites such as Choline, creatine, and others, and ratio of the peaks. See also Danielsen and Ross, Magnetic Resonance Spectroscopy Diagnosis of Neurological Diseases, Marcel Dekker, Inc. (1999); Ross, B. et al., *Magnetic Resonance Quarterly*, 10, 191-247 (1994); and Ross et al., U.S. Pat. No. 5,617,861. Based on the information in the above publications, as well as information available in the art, those of skill in the art should be able to practice the invention on all types of tumors in accordance with the present invention.

The present invention can be carried out in any suitable manner, for example, as follows. Prior to initiating a therapy on a patient, the tumor is localized. Thus, for example, magnetic resonance images (MRI's) of the tumor and the adjoining or surrounding normal tissue, e.g., brain metastasis, breast malignancy, or bone tumor, with axial, sagittal, and coronal T1 and T2 images are obtained with and without contrast. A region of interest (ROI) is selected. The ROI, in an embodiment, is a part or whole of the tumor and an adjoining or surrounding normal tissue recruited for angiogenesis. This can be carried out based on the MRI findings to determine the tumor volume and location to be studied. MR spectra of the ROI are obtained within or outside the tumor utilizing short and/or long TE (echo time), preferably short echo, pulse sequences. The spectra obtained are interpreted. The peak corresponding to Choline is identified, e.g., at a chemical shift of 3.22 ppm. Based on the Choline peak, the amount of total cellular membranes is determined from either the height of the peak or the area under the peak. An internal or external standard is identified in the ROI. An example of an internal standard is creatine or total creatine. An example of an external standard is 100% 2-(trimethylsilyl)-ethanol (TSE), which may be taped to the head coil of the MR spectrometer. Kreis, R. et al., *J. Magnetic Resonance*, Series B 102, 9-19 (1993). The ratio of the Choline to the standard is calculated. The Choline to creatine ratio represents a measure of the total cell membranes within the ROI of the tumor or outside the tumor prior to treatment.

The treatment of the tumor is initiated by administering an effective amount of the angiogenesis inhibitor starting from time zero. The early treatment response can be monitored, for example, at 24 hours (day 1) to 168 hours (day 7), as follows. The tumor is localized utilizing the same MRI pulse sequences as prior to the treatment. The same ROI is selected within and/or outside the tumor. MR spectra of the tumor are obtained utilizing the same pulse sequences, the same TR (relaxation time), TE (echo time), phases, and frequency averages. The MR spectra are interpreted as before and the Choline to creatine ratios (e.g., height or area ratios) are calculated.

If the observed decrease in the Choline to creatine ratio is 15% or more, preferably 20% or more, and more preferably 25% or more relative to pre-treatment condition, then it can be concluded that an early response is positive and angiogenesis has been stopped. The early decrease in the Choline, e.g., total choline, to creatine ratio identifies a decrease in the intracellular cell membranes, for example, a decrease in the number of organelles and their granules and/or vesicles. If the ratio of Choline to creatine increases, e.g., a 15% or more, preferably 20% or more, and more preferably 25% or more, of an early increase in the ratio is observed, the increase identifies an increase in the intracellular membranes, for example, an increase in the organelles and their granules and/or vesicles. A change (decrease) in the amount of Choline in the region adjoining or surrounding the region is indicative of inhibition of angiogenesis. A change (decrease) in the amount of Choline in the tumor is indicative of inhibition of the tumor. Thus, MRS can be used to study the early response or effectiveness of a cancer treatment, both in inhibiting the tumor itself and in the metastasis of tumor.

The present invention further provides a method for determining effectiveness of a molecule as a drug for treating cancer comprising administering an amount of the molecule to an animal having a cancerous tissue and measuring, by Magnetic Resonance Spectroscopy, the amount of Choline present in the cancerous tissue before and after administering the molecule, wherein the molecule comprises a angiogenesis inhibitor, whereby a decrease in the amount of Choline after administering the molecule is indicative of its effectiveness.

The animals that can be used in the present method can be, for example, mammals such as mice, rats, horses, guinea pigs, rabbits, dogs, cats, cows, pigs, monkeys, and humans. The amount of cell surface receptor inhibitor will vary with a number of factors, e.g., weight of the animal, type of cancer, and severity of cancer, and is within the skill of the artisan. The potential drug can be administered by any suitable route of administration, e.g., oral, aerosol, parenteral, subcutaneous, intravenous, intraarterial, intramuscular, interperitoneal, rectal, and vaginal routes. The cancer can be natural or induced. The effectiveness of a potential drug can be determined within a relatively short period of time, for example, within 12-168 hours, preferably 12-24 hours.

The present invention further provides a method for monitoring early treatment response of an angiogenesis effector treatment in a diseased animal comprising measuring, by MRS, the amount of Choline, e.g., total choline, present in the diseased tissue before and after treatment, wherein said treatment comprises administration of an angiogenesis effector, whereby a change in the amount of Choline after treatment is indicative of a positive response. The angiogenesis effector can inhibit angiogenesis or promote angiogenesis. Angiogenesis can be inhibited by interfering with a proangiogenic signaling pathway involving a growth factor, integrin/protease, coagulation/fibrinolysis factor, or inflammatory factor. Angiogenesis can be promoted by up-regulating a proangiogenic pathway involving a growth factor, integrin/protease, coagulation/fibrinolysis factor, or inflammatory factor It is contemplated that the present invention, in an embodiment, can be employed to monitor the early treatment response of any disease involving angiogenesis, i.e., non-neoplastic diseases where abnormal angiogenesis contributes to a disease or inducement of angiogenesis could lead to a treatment of disease, for example, cardiac disease, rheumatoid arthritis, retinopathy, hereditary hemorrhagic telangiectasia, and hyperplasia. For example, in a patient who had a stroke, a growth factor such as the VEGF can be administered to the patient (e.g., in the brain) and the development of new blood vessels can be monitored. Further, in cardiac patients, a growth factor such as VEGF, for example, through the use of a catheter to a location in the heart, and the development and growth of new vessels can be monitored. In diseases such as retinopathy and rheumatoid arthritis, the patient undergoing treatment with an angiogenesis inhibitor can be monitored for a decrease in the number or size of blood vessels contributing to the disease.

The following example further illustrates an embodiment of the invention, but of course should not be construed as in any way limiting its scope.

Example

This Example illustrates a method for measuring the ratio of Choline to creatine, in accordance with an embodiment of the invention. As illustrated in FIG. 1, a region of interest (ROI) and the individual voxels (V) are used to determine the amount of total choline (or Choline) in cell membranes. An axial T2 FLAIR (Fluid Attenuated Inversion Recovery) image identifies the location of the tumor. An ROI is prescribed to include the tumor, the surrounding white matter, and the normal contralateral white matter measuring 5 cm×8 cm. Forty spectra are obtained of the entire ROI using multi-voxel technique, with each voxel measuring 1 cm×1 cm to reduce partial volume averaging. A specific short-echo PRESS pulse sequence with a TR 1500 msec, TE 35 msec, 128 number of averages, with 24 phase and 24 frequency steps acquires the spectra in 9 minutes and 50 seconds. A software program generates spectra from selected voxels: V(N)=voxel of normal contralateral white matter, V(+A) =voxel of white matter undergoing angiogenesis, V(−A) =voxel of white matter not undergoing angiogenesis, V(T) =voxel within the tumor. Segments of the spectra showing the peak heights of total choline (Choline or CHO) and of creatine (CRE) are diagramed for V(N), V(+A), V(−A) and V(T). Choline to creatine ratios are generated (CHO/CRE) to quantify the cell membranes at each location. The V(N) identifies the CHO/CRE=1.0 representing the quantity of normal membranes. At V(+A) the CHO/CRE is increased 20% to 1.2. In V(−A) the CHO/CRE is similar to V(N). In the tumor V(T) the CHO/CRE is increased to 2.0 indicating twice the amount cell membranes at this location in the tumor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for monitoring early treatment response of a cancer treatment comprising measuring, by Magnetic Resonance Spectroscopy (MRS), the amount of Choline present in a tissue adjoining or surrounding the cancerous tissue before and after treatment, wherein said treatment comprises administration of an angiogenesis inhibitor, whereby a decrease in the amount of Choline after treatment is indicative of a positive response.

2. The method of claim 1, wherein the MRS is based on the resonance of nuclei selected from the group consisting of $^{31}$P, $^{1}$H, $^{13}$C, and $^{23}$Na, and any combination thereof.

3. The method of claim 2, wherein the MRS is based on $^{1}$H resonance.

4. The method of claim 1, wherein measuring the amount of Choline comprises measuring the height of a peak corresponding to Choline.

5. The method of claim 1, wherein measuring the amount of Choline comprises measuring the area under a peak corresponding to Choline.

6. The method of claim 1, wherein measuring the amount of Choline comprises measuring the ratio of the height of a peak corresponding to Choline relative to the height of peak of an internal standard.

7. The method of claim 6, wherein the internal standard is total creatine when the MRS is based on $^{1}$H resonance.

8. The method of claim 6, wherein the internal standard is adenosine triphosphate (ATP) when the MRS is based on $^{31}$P resonance.

9. The method of claim 1, wherein measuring the amount of Choline comprises measuring the ratio of the area under a peak corresponding to Choline relative to the area under a peak of an internal standard.

10. The method of claim 9, wherein the MRS is based on $^{1}$H resonance and the internal standard is total creatine.

11. The method of claim 1, wherein the angiogenesis inhibitor interrupts one or more pathways selected from the group consisting of a growth factor signaling pathway, an integrin/protease pathway, a coagulation/fibrinolysis pathway, and an inflammatory signaling pathway.

12. The method of claim 1, wherein measuring the amount of Choline comprises measuring the amount of choline, phosphocholine, phosphatidylcholine, lysophosphatidylcholine, or glycerophosphocholine, phosphomonoesters of choline, phosphodiesters of choline, phosphoethanolamine, glycerophosphoethanolamine, or any combination thereof.

13. The method of claim 1, wherein the amount of Choline is measured within a period of about 168 hours of said treatment.

14. The method of claim 13, wherein the amount of Choline is measured within a period of about 24 hours.

15. The method of claim 14, wherein the amount of Choline is measured within 12 hours of said treatment.

16. The method of claim 1, wherein the angiogenesis inhibitor is selected from the group consisting of VEGF receptor tyrosine kinase inhibitors, monoclonal antibodies to growth factor receptors, VEGF toxin conjugate, dominant negative VEGF-2, soluble VEGFR (VEGF-TRAP) and antisense oligonucleotides, growth factor transforming kinases, farnesyl transferase inhibitors, agents targeting tumor suppressors, agents that inhibit proliferation of endothelial cells, antibody and peptide integrin inhibitors, plasmin inhibitors, urokinase-type plasminogen activator inhibitors, matrix metalloproteinase inhibitors, cyclooxygenase inhibitors, lipoxygenase inhibitors, and inhibitors of mitogenic effects, and any combination thereof.

17. The method of claim 1, wherein the angiogenesis inhibitor is selected from the group consisting of SU5416, SU6668, cetuximab, gefitinib, erlotinib, canertinib, EKB-569, lapatinib, IMC-C225, ABX-EGF, HuMax-EGFR, DC101, suramin, gleevec, herceptin, p-53 (PRIMA-1), thalidomide, squalamine, anti-$\alpha_{v}B_{3}$ integrin antibody, anti-$\alpha_{v}B5$ integrin antibody, cyclic peptide inhibitor of integrin $\alpha_{v}B_{3}$// $\alpha_{v}B_{5}$, cilengitide, fumagallin, TNP-470, EMD 121974, $\alpha$2-antiplasmin, $\alpha$2-macroglobulin, kininostatin, BMS275291, COL-3, marimastat, neovastat, solimastat, angiostatin, endostatin, antithrombin fragments, fibrinogen-E, fibrin-D, thrombospondin-1, platelet factor-4, low molecular weight heparins, Vioxx, Celebrex, and interferon-$\alpha$ and $\beta$, and any combination thereof.

18. The method of claim 1, wherein the cancer is selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, gastric cancer, pancreatic cancer, neuroblastoma, mesothelioma, prostate cancer, bone cancer, kidney cancer, and hepatocellular cancer.

19. The method of claim 1, wherein inhibition of angiogenesis causes an interruption in an up-regulated intracellular organelle.

20. The method of claim 19, wherein the interruption in the up-regulated intracellular organelle decreases the number of secretory granules.

21. The method of claim 19, wherein the interruption in the up-regulated intracellular organelle decreases the number of transporting vesicles.

22. The method of claim 1, wherein inhibition of angiogenesis causes an interruption in a function of the Golgi apparatus.

23. The method of claim 1, wherein inhibition of angiogenesis causes an interruption in a function of the lysosomes.

24. The method of claim 1, wherein inhibition of angiogenesis causes an interruption in a function of the endoplasmic reticulum.

25. The method of claim 1, wherein inhibition of angiogenesis causes an interruption in a function of the mitochondrion.

26. The method of claim 1, wherein inhibition of angiogenesis causes an interruption in a function of the nucleus.

27. The method of claim 1, wherein inhibition of angiogenesis causes an interruption in a function of the peroxisomes.

28. A method for monitoring cancer treatment comprising: (a) localizing a tumor in a patient; (b) selecting a region of interest (ROI) of the tumor and a tissue adjoining or surrounding the tumor; (c) obtaining magnetic resonance spectra (MRS) of the ROI; (d) measuring the amount of Choline from the MRS spectra; (e) initiating treatment comprising administering an angiogenesis inhibitor; (f) obtaining MR spectra of the tumor at the same ROI within a period of 7 days of initiating treatment; (g) measuring the amount of Choline from the MR spectra; and (h) comparing the amount of Choline obtained before treatment with the amount of Choline obtained after treatment; whereby a decrease in the amount of Choline after treatment is indicative of a positive response to treatment.

29. The method of claim 28, wherein the MR spectra of the tumor is obtained within 3 days of initiating treatment.

30. The method of claim 29, wherein the MR spectra of the tumor is obtained within 1 day of initiating treatment.

31. A method for determining effectiveness of a molecule as a drug for treating cancer comprising administering an amount of the molecule to an animal having a cancerous tissue and measuring, by Magnetic Resonance Spectroscopy, the amount of Choline present in the tissue surrounding the cancerous tissue before and after administering the molecule, wherein said molecule comprises an angiogenesis inhibitor, whereby a decrease in the amount of Choline after administering said molecule is indicative of its effectiveness.

32. A method for monitoring early treatment response of an angiogenesis effector treatment in a diseased animal comprising measuring, by Magnetic Resonance Spectroscopy (MRS), the amount of Choline present in the diseased tissue before and after treatment, wherein said treatment comprises administration of an angiogenesis effector, whereby a change in the amount of Choline after treatment is indicative of a positive response.

33. The method of claim 32, wherein the angiogenesis effector is an inhibitor of angiogenesis.

34. The method of claim 32, wherein the angiogenesis effector is a promoter of angiogenesis.

35. The method of claim 33, wherein the disease is retinopathy, rheumatoid arthritis, hereditary hemorrhagic telangiecstasia, or hyperplasia.

36. The method of claim 34, wherein the disease is a stroke or cardiac disease.

37. The method of claim 33, wherein angiogenesis is inhibited by interfering with a proangiogenic signaling pathway involving a growth factor, integrin/protease, coagulation/fibrinolysis factor, or inflammatory factor.

38. The method of claim 34, wherein angiogenesis is promoted by up-regulating a proangiogenic pathway involving a growth factor, integrin/protease, coagulation/fibrinolysis factor, or inflammatory factor.

39. The method of claim 1, wherein the Choline is the total choline.

40. The method of claim 28, wherein the Choline is the total choline.

41. The method of claim 31, wherein the Choline is the total choline.

42. The method of claim 32, wherein the Choline is the total choline.

* * * * *